US00PP31768P2

(12) United States Plant Patent
Hoogenraad

(10) Patent No.: US PP31,768 P2
(45) Date of Patent: May 19, 2020

(54) ***VACCINIUM* PLANT NAMED 'HOOGI045'**

(50) Latin Name: *Vaccinium corymbosum*
Varietal Denomination: Hoogi045

(71) Applicant: Mark Sebastiaan Hoogenraad, Ederveen (NL)

(72) Inventor: Mark Sebastiaan Hoogenraad, Ederveen (NL)

( * ) Notice: Subject to any disclaimer, the term of this patent is extended or adjusted under 35 U.S.C. 154(b) by 0 days.

(21) Appl. No.: 16/501,299

(22) Filed: Mar. 21, 2019

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — Penny J. Aguirre

(57) ABSTRACT

A new cultivar of *Vaccinium* plant, 'Hoogi045', that is characterized by its young foliage that is variegated bright pink, salmon pink and green when young and variegated with creamy white and green when mature, its abundant berries that are that are sweet in taste.

3 Drawing Sheets

CROSS REFERENCE TO A RELATED APPLICATION

This application is related to plant breeders' rights application filed in Europe on May 10, 2017, application No. 2017/1278. There have been no offers for sale anywhere in the world prior to the effective filing date of this Application. Plants were not accessible to one of ordinary skill in the art. Plants could not have been derived from the printed plant breeder's rights documents.

Botanical classification: *Vaccinium corymbosum.*

Cultivar designation: 'Hoogi045'.

BACKGROUND OF THE INVENTION

The present invention relates to a new and distinct cultivar of *Vaccinium corymbosum*, and will be referred to hereafter by its cultivar name, 'Hoogi045'. 'Hoogi045' is a new cultivar of northern highbush blueberry grown for use as a fruit bearing landscape shrub.

'Hoogi045' was discovered by the Inventor as a chance seedling in a nursery bed in Ederveen, The Netherlands in May of 2011. The exact parentage is unknown, however it is most likely a seedling of open pollinated 'Bluecrop' based on its characteristics and its proximity to the new cultivar as the nursery bed was planted with 'Bluecrop'.

Asexual propagation of the new cultivar was first accomplished by the Inventor by stem cuttings in Ederveen, The Netherlands in 2016. Asexual propagation by stem cuttings has determined that the characteristics of this cultivar are stable and are reproduced true to type in successive generations.

SUMMARY OF THE INVENTION

The following traits have been repeatedly observed and represent the characteristics of the new cultivar, which in combination distinguish 'Hoogi045' as a new and distinct cultivar of *Vaccinium.*

1. 'Hoogi045' exhibits foliage that is variegated bright pink, salmon pink and green when young and variegated with creamy white and green when mature.
2. 'Hoogi045' exhibits abundant fruit.
3. 'Hoogi045' exhibits berries that are sweet in taste.

'Bluecrop', the likely parent plant of 'Hoogi045', is similar to 'Hoogi045' in plant size and plant habit. 'Bluecrop' differs from 'Hoogi045' in having foliage that are only green in color. 'Hoogi045' can also be compared to the cultivar 'VacBril' (U.S. Plant Pat. No. 30,087). 'VacBril' is similar to 'Hoogi045' in having uniquely colored foliage. 'VacBril' differs from 'Hoogi045' in having foliage that is dark purple in spring and becomes mottled with dark purple and green during the growing season.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to website listings on plantipp.eu, crocus.co.uk, and plantarium.nl (award competition).

BRIEF DESCRIPTION OF THE DRAWINGS

The accompanying colored photographs illustrate the overall appearance and distinct characteristics of the new *Vaccinium*. The photographs were taken of a 2.5-year-old plant as grown outdoors in a 30-cm container (after a single early spring pruning) in Ederveen, The Netherlands.

The photograph in FIG. 1 provides a side view of 'Hoogi045'.

Figure 1:
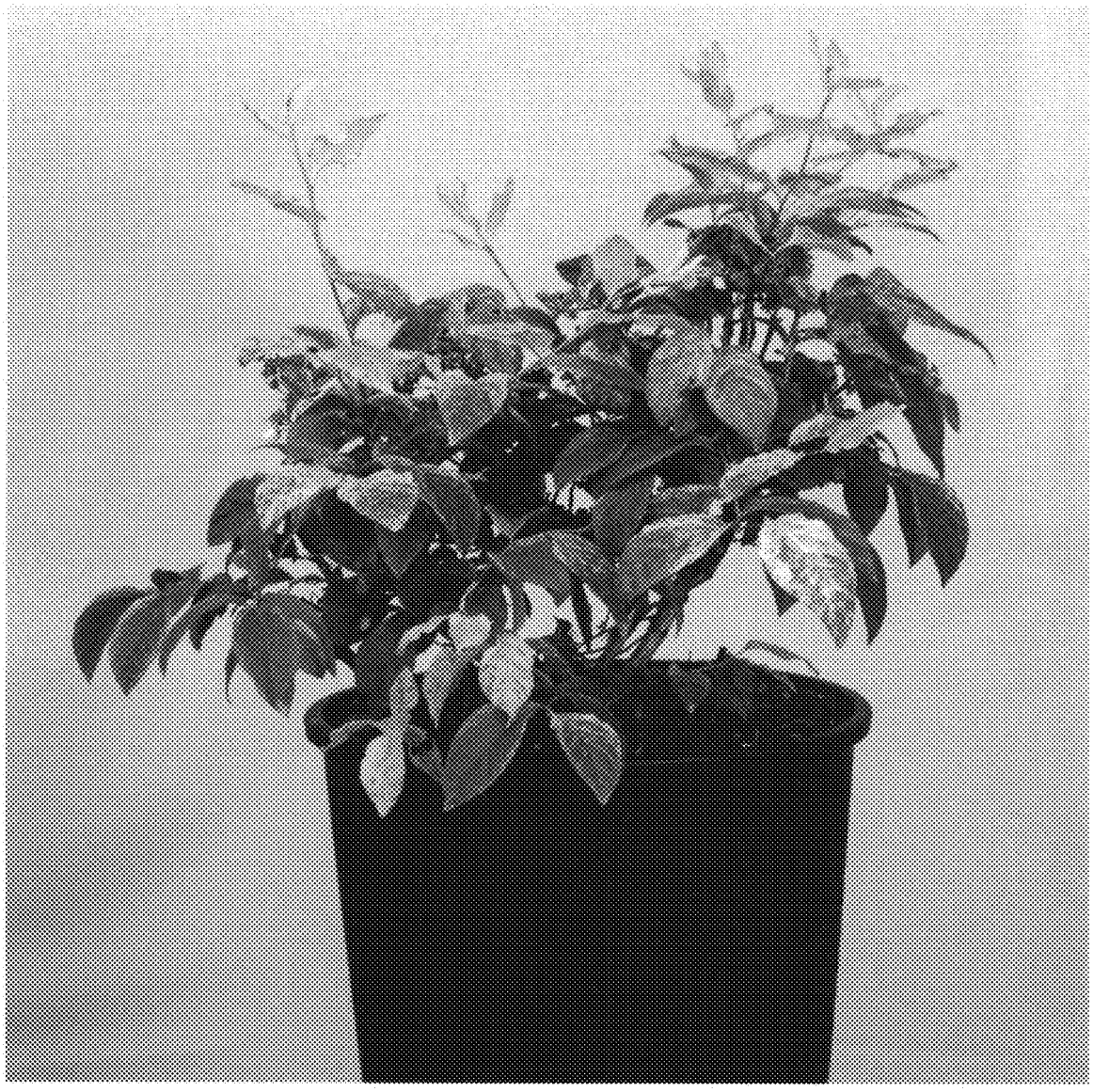
Figure 2:
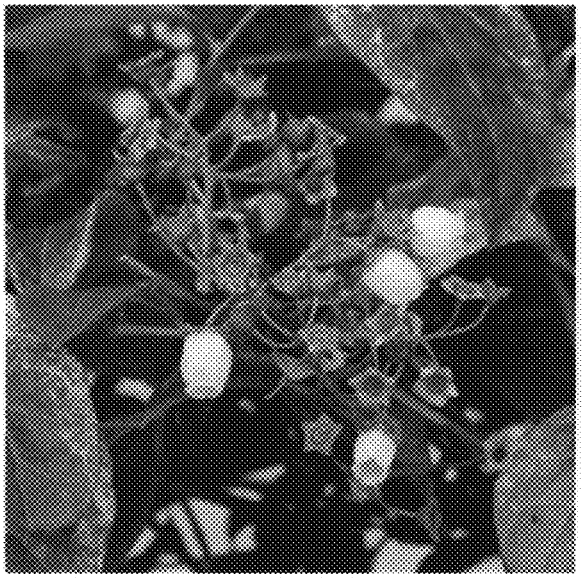

The photograph in FIG. 2 provides a view of an inflorescence of 'Hoogi045'.

Figure 3:
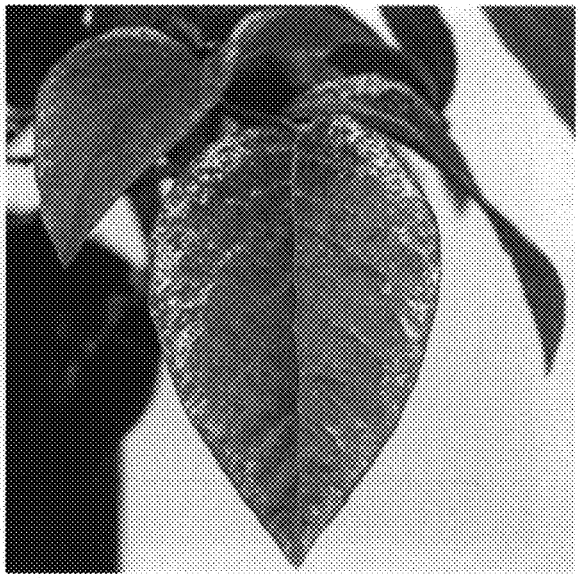

The photograph in FIG. 3 provides a close-up view of the mature foliage of 'Hoogi045'.

Figure 4:
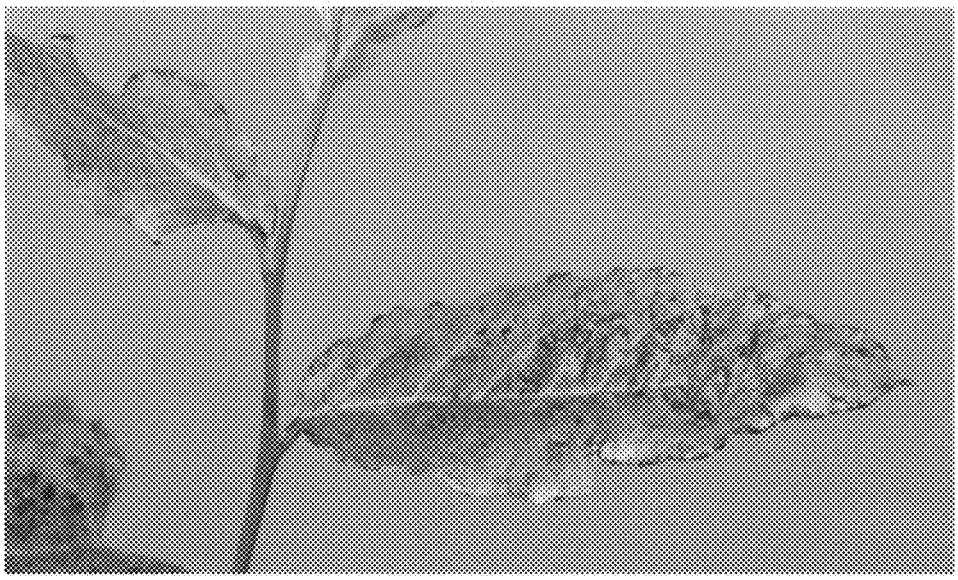

The photograph in FIG. 4 provides a close-up view of the young foliage 'Hoogi045'.

Figure 5:
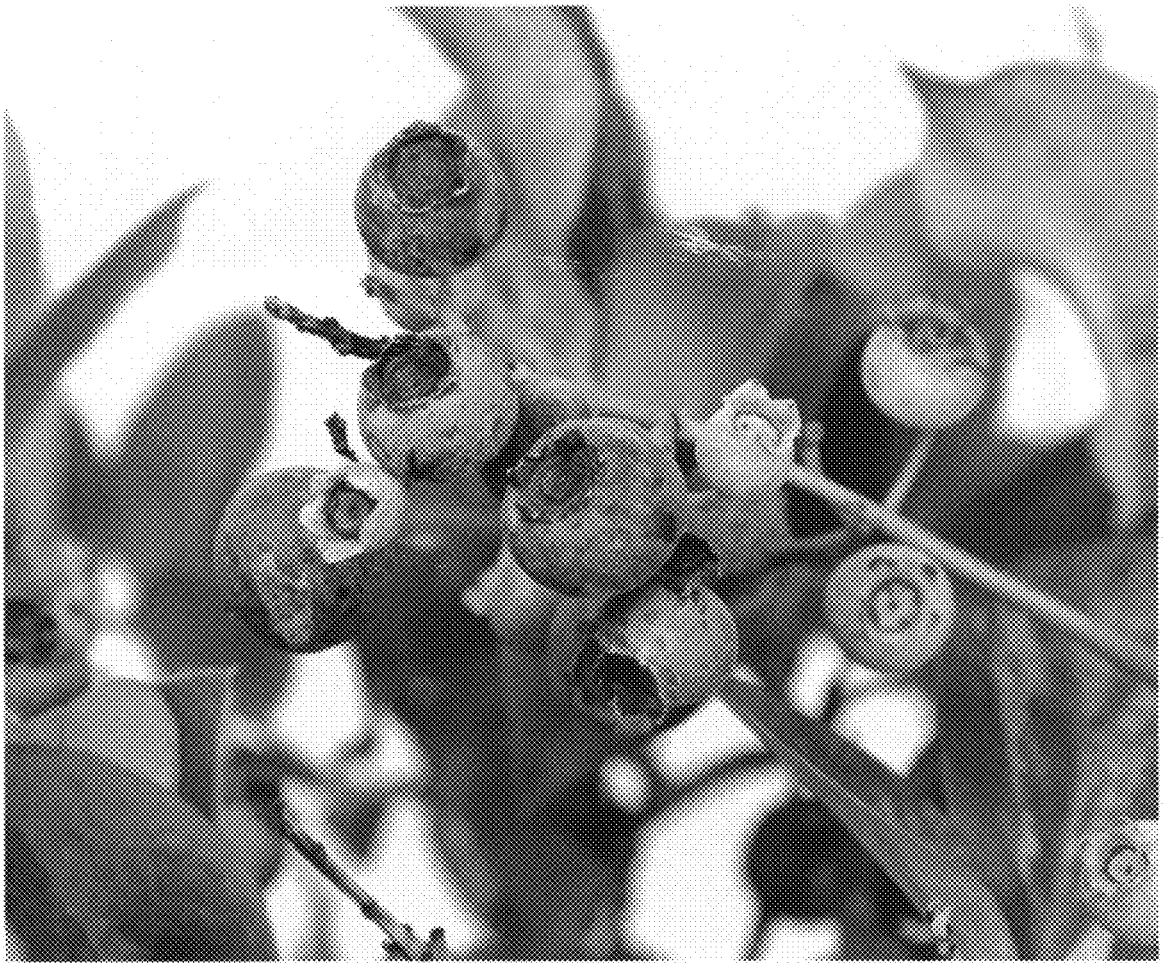

The photograph in FIG. 5 provides a view of the berries of 'Hoogi045'.

The colors in the photographs may differ slightly from the color values cited in the detailed botanical description, which accurately describe the colors of the new *Vaccinium*.

DETAILED BOTANICAL DESCRIPTION OF THE PLANT

The following is a detailed description of 2.5-year-old plants as grown outdoors in 30-cm containers (with a single early spring pruning) in Ederveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General plant characteristics:

*Plant type.*—Deciduous fruit bearing shrub.

*Plant habit.*—Broad spreading and upright.

*Height and spread.*—Reaches an average of 1 m in height and 70 cm in width as a mature plant.

*Hardiness.*—Hardy in at least U.S.D.A. Zones 4 to 8.

*Disease and pests resistance.*—No susceptibility or resistance to diseases or pests has been observed.

*Environmental conditions.*—High tolerance to rain, and moderate tolerance to wind.

*Root description.*—Fibrous.

*Growth rate.*—Moderate.

*Propagation.*—Stem cuttings.

*Root development.*—A cutting will root in a about 3 months, a young rooted plant will finish from a rooted cutting in a P9 container in about 6 months.

Stem description:

*Current year's growth.*—Flattened in shape, young; a color between 139D and 145A, mature; 138B (internodes and nodes).

*Dormant stems* (*previous year's growth*).—Rounded in shape, a blend of 166B, 200D, and N200B in color.

*Stem size.*—Lateral branched an average of 17 cm in length and 3 mm in width.

*Internode length.*—An average of 2.2 cm.

*Branching.*—Well branched, 7 main basal branches and 42 lateral branches per plant.

*Stem aspect.*—Held at an average of 50° to vertical.

*Stem strength.*—Strong.

*Suckering.*—Medium.

Foliage description:

*Leaf shape.*—Elliptic.

*Leaf division.*—Simple.

*Leaf base.*—Attenuate to rounded.

*Leaf apex.*—Acute.

*Leaf venation.*—Pinnate, color mature leaves; upper surface 146C, lower surface 138B.

*Leaf margins.*—Entire.

*Leaf attachment.*—Petiolate.

*Leaf arrangement.*—Alternate.

*Leaf number.*—An average of 8 per lateral branch.

*Leaf orientation.*—Flat to slightly convexed.

*Leaf surface.*—Upper and lower surface smooth and glabrous with main vein on upper surface pubescent with short adpressed hairs; about 0.2 mm in length, and too fine to measure with color chart, upper surface nonrugose, lower surface slightly rugose.

*Leaf color.*—Variegated, newly expanded leaves upper surface; 48A and 180C, newly expanded leaves lower surface; 181D, mature and fall upper surface; a color between 137A and 146A and marbled and dusted with 150D and 48C to 48D at base, mature and fall color lower surface; 138B and marbled and dusted with 150D and 49B to 49C at base.

*Leaf size.*—Average of 9.5 cm in length and 4.9 cm in width.

*Petioles.*—Round in shape, an average of 3 mm in length and 2 mm in width, 144B in color, glabrous and matt surface.

*Stipules.*—None observed.

Inflorescence description:

*Blooming period.*—Early summer in The Netherlands.

*Inflorescence.*—Axillary raceme, average of 5.5 cm in length 4.9 cm in width.

*Lastingness of inflorescence.*—Average of 28 days but highly dependent on temperatures, individual flowers last about one week.

*Number of flowers.*—Average of 8 per inflorescence and 240 per plant.

*Flower buds.*—Ovate in shape and 5-ribbed, 1.1 cm in length and 6 mm in width, smooth, glabrous, and velvety surface, NN155B in color and 145C at apex.

*Flower fragrance.*—Slight, sweet.

*Flower size.*—Average of 1.2 cm in length and 9 mm in width.

*Corolla.*—Urceolate in shape, comprised of 5 fused petals with tip free, acute, and curled under with entire margin, average of 1 cm in length and 8 mm in width, base of free tip 3 mm in diameter, color on both surfaces when opening NN155A to NN155B and tinged at apex with 157C to 157D, color on both surfaces when mature NN155C to NN155D and tinged at apex with 157C to 157D, surface smooth, glabrous, moderately velvety on both surfaces, self-cleaning.

*Calyx.*—Campanulate, un-fused, an average of 3 mm in length and 9 mm in diameter.

*Sepals.*—5, average of 2.5 mm in length and 4 mm in diameter, deltoid in shape, broadly acute apex, broadly cuneate base, entire margin, color when opening lower surface; 138C, color when fully open upper surface; 143C, color when fully open lower surface; 138C, smooth and glabrous surface on both surfaces.

*Peduncles.*—Round, strong, an average of 3.8 cm in length and 1.5 mm in diameter, 143B to 143C in color, glabrous, slightly glossy and smooth surface, held at an angle of 55° to lateral axis.

*Pedicels.*—Round, moderately strong, an average of 1.2 cm in length and 1 mm in diameter, 143C in color, slightly glossy and smooth surface, held at an angle of 70° to peduncle axis.

Reproductive organs:

*Androecium.*—10 stamens, filaments; 157B in color and 3 mm in length, anthers; dorsifixed, linear in shape, 165B in color, 2.5 mm in length, 0.5 mm in width, pollen is very low in quantity and too minimal to record color reading.

*Gynoecium.*—Pistil; 1, 8.5 mm in length, stigma; club-shaped, 0.5 mm in length and width, 145C to 145D in color, style; 8 mm in length, 145B in color, ovary; 138B in color.

Fruit description:

*Type.*—Berry.

*Number.*—240 per plant.

*Fruit size.*—Average of 1.2 cm in length, 1.4 cm in diameter.

*Fruit texture.*—Glabrous, covered with a thin waxy layer.

*Fruit color.*—203C, waxy layer 115C and 202B.

*Fruit taste.*—Sweet, non-acidic.

*Fruit ripening.*—Average of 2 months.

*Fruit keeping.*—Average of 1 month.

*Seed quantity.*—Average of 20 per fruit.

*Seed size.*—Average of 1.5 mm in length, 1 mm in diameter.

*Seed texture.*—Smooth and glabrous.

*Seed color.*—164A.

It is claimed:

1. A new and distinct cultivar of *Vaccinium* plant named 'Hoogi045' as herein illustrated and described.

* * * * *